(12) United States Patent
Lee et al.

(10) Patent No.: US 11,439,747 B2
(45) Date of Patent: Sep. 13, 2022

(54) DRUG DELIVERY DEVICE AND METHOD

(71) Applicant: Purdue Research Foundation, West Lafayette, IN (US)

(72) Inventors: Hyowon Lee, West Lafayette, IN (US); Bahar Dhowan, So. Barrington, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/152,063

(22) Filed: Oct. 4, 2018

(65) Prior Publication Data

US 2019/0125966 A1 May 2, 2019

Related U.S. Application Data

(60) Provisional application No. 62/568,096, filed on Oct. 4, 2017.

(51) Int. Cl.
*A61M 5/142* (2006.01)
*A61M 31/00* (2006.01)
(Continued)

(52) U.S. Cl.
CPC ....... *A61M 5/14276* (2013.01); *A61B 5/4839* (2013.01); *A61B 5/4845* (2013.01); *A61B 5/4848* (2013.01); *A61K 9/0024* (2013.01); *A61K 9/0097* (2013.01); *A61M 5/44* (2013.01); *A61M 31/002* (2013.01);
(Continued)

(58) Field of Classification Search
CPC ................ A61M 5/14276; A61M 5/44; A61M 2205/0288; A61M 31/002; A61M 5/14244; A61M 2205/04; A61M 2205/0272; A61M 2205/3507; A61M 2205/3303; A61M 2205/3515; A61B 5/4839; A61B 5/6861; A61K 9/0024; A61K 9/0009; A61K 41/00;
(Continued)

(56) References Cited

U.S. PATENT DOCUMENTS 5,170,801 A * 12/1992 Casper ..................... A61B 5/42
604/113
6,394,997 B1 * 5/2002 Lemelson ............ A61K 9/0009
604/890.1

(Continued)

OTHER PUBLICATIONS

Boscarion, J.A., Rukstalis, M., Hoffman, S.N., Han, J.J., Erlich, P.M., Gerhard, G.S., and Stewart, W.F., (2010), Risk factors for drug dependence among out-patients on opiod therapy in a large US health-care system; Addiction, 105(10), 1776-1782.
Strang, J., Kelleher, M., Best, D., Mayet, S., and Manning, V., (2006), Emergency naloxone for heroin overdose; BMJ (Clinical Research Ed.), 333 (7569), 614-5.
Piper, T.M., Stancliff, S., Rudenstine, S., Sherman, S., Nandi, V., Clear, A., and Galea, S., (2009); Evaluation of a Naloxone Distribution and Administration Program in New York City; http://dx.doi.org/10.1080/10826080701801261.

*Primary Examiner* — Kevin C Sirmons
*Assistant Examiner* — Alexandra Lalonde
(74) *Attorney, Agent, or Firm* — Hartman Global IP Law; Gary M. Hartman; Domenica N.S. Hartman

(57) ABSTRACT

An implantable drug delivery device and method for delivering a drug to a living body. The device includes a housing having at least one opening, a reservoir within the housing adapted to contain a drug, a temporary seal closing the opening of the housing, and a heating element in thermal contact with the temporary seal. The heating element is adapted to generate heat in response to a magnetic field to melt the temporary seal and release a drug within the reservoir through the opening of the housing.

13 Claims, 5 Drawing Sheets

(51) Int. Cl.
  *A61B 5/00* (2006.01)
  *A61M 5/44* (2006.01)
  *A61K 9/00* (2006.01)
  *A61M 37/00* (2006.01)
  *A61K 31/485* (2006.01)
  *A61B 5/01* (2006.01)

(52) U.S. Cl.
  CPC ........... *A61M 37/0069* (2013.01); *A61B 5/01* (2013.01); *A61F 2250/0068* (2013.01); *A61K 31/485* (2013.01)

(58) Field of Classification Search
  CPC .............. A61K 41/0028; A61K 9/0053; A61K 9/0065
  See application file for complete search history.

(56) References Cited

U.S. PATENT DOCUMENTS

| | | | | |
|---|---|---|---|---|
| 10,086,138 | B1* | 10/2018 | Novak, Jr. | G16H 20/17 |
| 2002/0055734 | A1* | 5/2002 | Houzego | A61M 31/002 |
| | | | | 604/891.1 |
| 2007/0106266 | A1* | 5/2007 | Hood | A61K 9/0009 |
| | | | | 604/20 |
| 2007/0196281 | A1* | 8/2007 | Jin | A61N 2/06 |
| | | | | 424/9.34 |
| 2011/0212163 | A1* | 9/2011 | Hoare | A61P 35/00 |
| | | | | 424/450 |
| 2017/0325746 | A1* | 11/2017 | Niichel | A61K 31/00 |
| 2019/0125687 | A1* | 5/2019 | Bielski | A61K 9/5031 |
| 2019/0231707 | A1* | 8/2019 | Stiles | A61K 31/485 |

* cited by examiner

DRUG DELIVERY DEVICE AND METHOD

CROSS REFERENCE TO RELATED APPLICATIONS

This application claims the benefit of U.S. Provisional Application No. 62/568,096 filed Oct. 4, 2017, the contents of which are incorporated herein by reference.

BACKGROUND OF THE INVENTION

The present application relates to drug delivery devices and methods. The invention particularly relates to single-use drug delivery devices that are implantable and suitable for delivering drugs, including but not limited to anti-overdose drugs to treat opioid overdoses.

This section introduces aspects that may help facilitate a better understanding of the disclosure. Accordingly, these statements are to be read in this light and are not to be understood as admissions about what is or is not prior art.

From 1999 to 2014, more than 165,000 people died in the U.S. from overdoses related to prescription opioids. This statistic would be much greater if deaths caused by illicit drugs were included. There exists an FDA-approved anti-overdose drug such as naloxone to counteract the action of opioids. Although naloxone availability has improved in recent years with legislation allowing for over-the-counter purchase of the drug, patients often are incapacitated to administer the potentially lifesaving drug to themselves in a timely manner. Therefore, there is a need for drug delivery devices and methods by which a person can quickly administer, and in some cases automatically or self-administer, an antidote to combat the effects of an overdose.

BRIEF DESCRIPTION OF THE INVENTION

The present invention provides implantable drug delivery devices and drug delivery methods suitable for a delivering drug to a living body in which the device is implanted.

According to one aspect of the invention, an implantable drug delivery device for delivering a drug to a living body includes a housing having at least one opening, a reservoir within the housing adapted to contain a drug, a temporary seal closing the opening of the housing, and a heating element in thermal contact with the temporary seal. The heating element is adapted to generate heat in response to a magnetic field to melt the temporary seal and release a drug within the reservoir through the opening of the housing.

Another aspect of the invention is a method of using an implantable drug delivery device of the type described above to deliver a drug to a living body in which the device is implanted.

Technical aspects of the device and method described above preferably include the ability to quickly administer, and in some cases automatically administer or self-administer, an antidote to combat the effects of an overdose.

Other aspects and advantages of this invention will be further appreciated from the following detailed description.

DETAILED DESCRIPTION OF THE INVENTION

Figure 1:
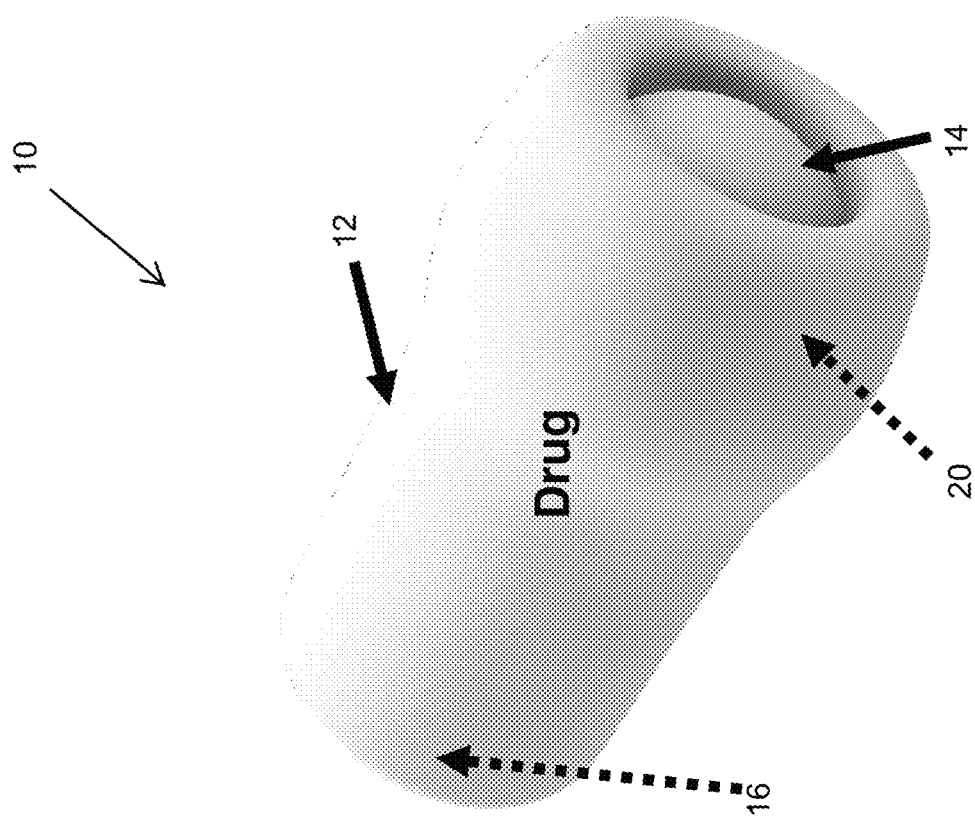
FIG. 1 schematically represents a nonlimiting embodiment of a drug delivery device adapted to deliver an antidote to combat the effects of an overdose in accordance with certain nonlimiting aspects of the invention.

For the purpose of promoting an understanding of certain aspects of the invention, reference is made below to certain nonlimiting embodiments illustrated in the drawings and specific language will be used to describe the same. It will nevertheless be understood that no limitation to the scope of the invention is thereby intended. Furthermore, any dimensions or relative scaling within or among any of the drawings is by way of example and not to be construed as limiting.

The following describes a drug delivery device capable of be implanted into a living body (hereinafter, "recipient") and distributing a drug into the tissue or bloodstream of the recipient, in some cases instantly distributing the drug, as a result of the device being triggered or activated in response to an overdose, and in some cases automatically triggered or activated by the detection of an overdose. As used herein, the term "implantable" is understood to mean a device having an appropriate size, construction, and composition to be able to be surgically placed in a recipient and remain within that recipient over an extended period, for example, thirty days or more, and potentially for the life of the recipient in which it is implanted. Particular but nonlimiting examples of drugs that can be delivered include antidotes such as naloxone, known for its use in the treatment of overdoses due to opioids, though the device could be used to deliver a wide variety of drugs, including emergency drugs (e.g., epinephrine for allergic reaction) and slow-release drugs (e.g., naltrexone for drug recovery treatment). The triggering event used to trigger or activate the device can be based on one or more normal reactions of the human body that may be observable or measurable. For example, when an overdose occurs, the human body reacts with a sudden increase in temperature and other abrupt changes to normal body functions. These sudden changes can be automatically sensed and used to automatically trigger the device, or observed to enable the recipient or others to manually trigger the device. Because the device is already implanted in the recipient, the device is able to immediately release the drug into the recipient to diffuse the overdose before lethal effects occur. The drug delivery device can be configured for subcutaneous implantation via a minimally invasive surgical procedure. Through such a device, it may be possible to eliminate the symptoms and effects of an overdose altogether.

Figure 2:
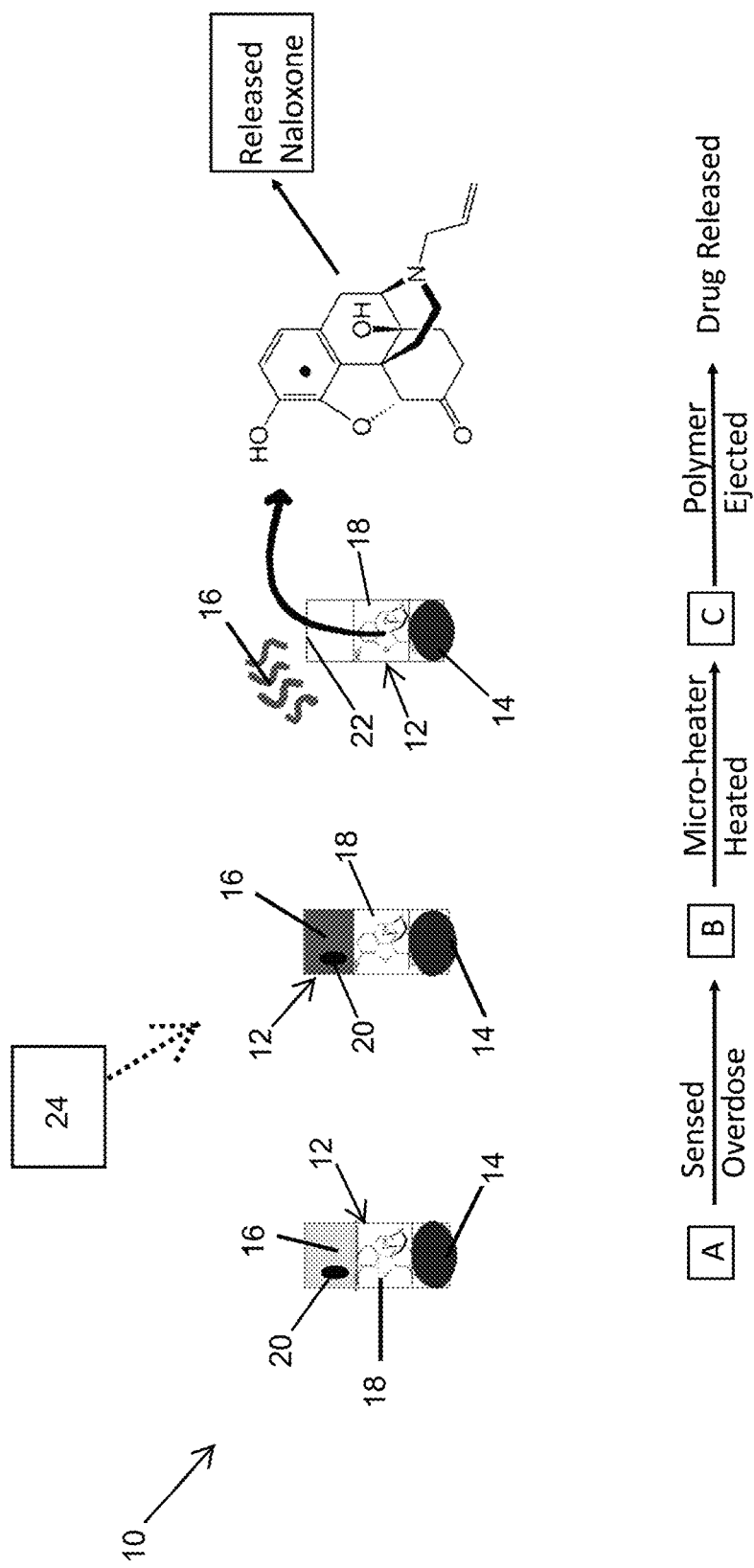
FIG. 2 schematically represents a process by which a drug delivery device, such as represented in FIG. 1, can be implanted and operated to sense an overdose and deliver a drug in accordance with certain nonlimiting aspects of the invention.

FIGS. 1 and 2 schematically represent a drug delivery device 10 adapted to deliver an antidote to combat the effects of an overdose. The device 10 is represented in FIG. 1 as comprising a housing 12 that defines a fluid-tight chamber or reservoir 18 (not visible in FIG. 1) within the device 10 that is capable of reliably containing a drug until its intended release from the device 10. The reservoir 18 is represented in FIG. 2 as a single compartment that contains a single dose of a single drug, though it is within the scope of the invention to compartmentalize the reservoir 18 to enable it to contain multiple doses of one or more drugs. Drugs contained within the reservoir 18 may be in liquid form, solid (e.g., powder) form, or a combination thereof. The housing 12 is represented as having oppositely-disposed ends, each closed to define the reservoir 18 within the housing 12. In the embodiment of FIGS. 1 and 2, a first end of the housing 12 has an opening that is closed with a permanent or persistent seal 14, though it is foreseeable that the housing 12 could be fabricated so that the first end is closed by an integral wall of the housing 12. The oppositely-disposed second end of the housing 12 has an opening 22 (not visible in FIG. 1) that is closed with a temporary seal 16 (not visible in FIG. 1), such that in combination the housing 12, the seal 14 (if present), and the temporary seal 16 define the fluid-tight reservoir 18. In any event, a drug within the reservoir 18 is not released unless, in the case of the particular embodiment shown in FIGS. 1 and 2, the temporary seal 16 sufficiently degrades to allow the drug to exit the reservoir 18 through the opening 22 in the housing 12. A heating element 20 (not visible in FIG. 1) is incorporated into the housing 12 so as to be in thermal contact or communication with the temporary seal 16, for example, embedded in the temporary seal 16 (FIG. 2), or a tubular-shaped heating element within the reservoir 18 adjacent the persistent seal 14 (FIG. 1) or adjacent the temporary seal 16. In each case, physical degradation of the seal 16 is the result of the seal 16 being sufficiently heated to soften or melt to the extent that the drug is able to exit the reservoir 18 through the opening 22 that had been previously closed by the seal 16.

FIG. 2 schematically represents steps by which the drug delivery device 10 can be triggered to release a drug contained in its reservoir 18. After the device 10 is subcutaneously implanted in a recipient, the device 10 remains dormant until such time as a physiological symptom of an overdose is observed or sensed, for example, as a result of an abrupt change in the recipient's body temperature as sensed by a temperature sensor (not shown) attached to or carried in proximity to the recipient's body. The detected or observed change serves as the basis for energizing the heating element 20. The heating element 20 sufficiently heats the temporary seal 16 to cause the seal 16 to physically degrade, for example, melt, and become at least partially dislodged from the end of the housing 12. The resulting opening 22 at the end of the housing 12 exposes the reservoir 18, allowing or forcing the drug to exit the reservoir 18. The heating element 20 may be heated to completely or only partially remove the seal 16 to regulate the release of the drug and, in some cases, heating may be discontinued to allow the seal 16 to resolidify and reseal the opening 22. These aspects of the invention may be promoted by choosing materials for the seal 16 that exhibit changes in permeability or porosity in response to the thermal stimulus provided by the heating element 20.

Suitable materials for the temporary seal 16 include, but are not limited to, biocompatible thermosensitive polymers, for example, cross-linked polymers such as waxes that have melting points above the normal body temperature of the recipient (e.g., about 40 to about 42° C.), enabling the seal 16 to at least partially melt into liquid form at a temperature well above normal for the human body and yet sufficiently low to not damage the tissue in which the device 10 is implanted. The drug may be contained within the reservoir 18 under pressure, such that the drug is forcibly ejected from the reservoir 18 once the seal 16 has sufficiently degraded.

The housing 12 and persistent seal 14 of the device 10 can be formed of materials having much higher melting or degradation temperatures than the seal 16. As nonlimiting examples, the housing 12 may be in the form of a polytetrafluoroethylene (PTFE) tube and the seal 14 formed of a PTFE body placed in one end of the PTFE tube of the housing 12. Alternatively, other materials can be used, or the housing 12 and seal 14 may be a unitary member formed of a single material. In one experimental embodiment, the housing 12 had a cylindrical shape with a length of about 10 mm and an outer diameter of about 4 mm to facilitate subcutaneous implantation of the device 10.

Figure 3:
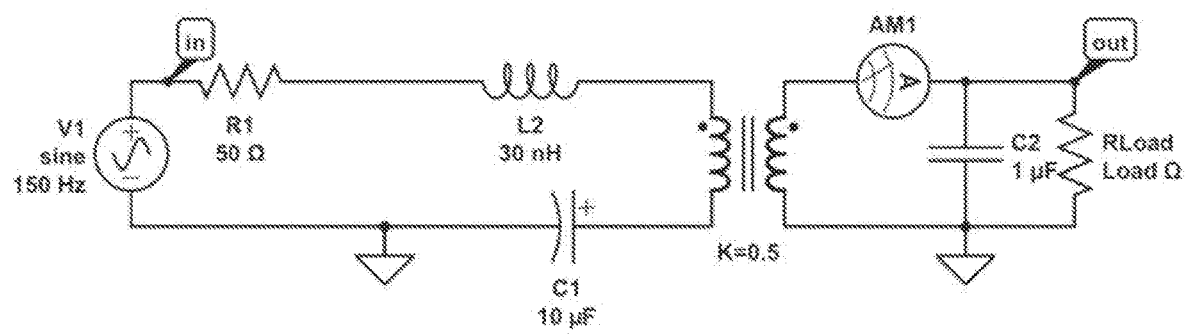
FIG. 3 schematically represents a nonlimiting embodiment of a circuit diagram of an impedance-matched primary and secondary coil design for providing inductively-coupled power transfer in a drug delivery device in accordance with certain aspects of the invention.

Examples of suitable devices for use as the heating element 20 include, but are not limited to, one or more ferrous (e.g., stainless steel) elements that can be heated by induction heating, and/or one or more ferrite elements with LC circuitry that enable the element to be heated by magnetic hysteresis. In FIG. 2, the heating element 20 is represented as being subjected to an oscillating magnetic field generated by a radio frequency (RF) generator 24, such that the heating element 20 can be wirelessly energized with RF waves at a resonant frequency of its circuitry. FIG. 2 generically represents the heating element 20 as inductively coupled to the generator 24, for example, as a result of the heating element 20 being a stainless steel element. FIG. 3 represents an embodiment utilizing a ferrite heating element 20, in which an impedance-matched primary and secondary coil design is used to achieve inductively coupled power transfer between circuitry of an RF generator (lefthand side of FIG. 3) and the LC circuitry (righthand side of FIG. 3) of the ferrite heating element 20. The generator 24 may be in the possession of the recipient, a caregiver or emergency responders, or may be attached to or carried by the recipient. In any case, the generator 24 is utilized to externally generate an emission capable of wirelessly energizing the heating element 20 to heat the temporary seal 16.

On the basis of the above, the delivery device 10 is adapted to be implanted in a human recipient (or other living body) to deliver one or more drugs to the recipient by releasing the drug contained in the reservoir 18 as a result of the heating element 20 generating heat in response to means that will typically be located outside the recipient's body. In the case of an overdose, the heating element 20 is energized upon the detection of physiological indications that can be observed, sensed, or otherwise detected in the recipient. The device 10 can be implanted under the skin of an at-risk patient of opioid misuse to enable immediate delivery of an antidote to the patient. In some cases, the device 10 may be triggered by others, such as a caregiver or emergency responder, though it is also foreseeable that the patient may be able to trigger the device 10 without assistance. As previously noted, it is also foreseeable that one or more sensors can be utilized to provide feedback control to automatically release the drug when overdose is detected.

Figure 4:
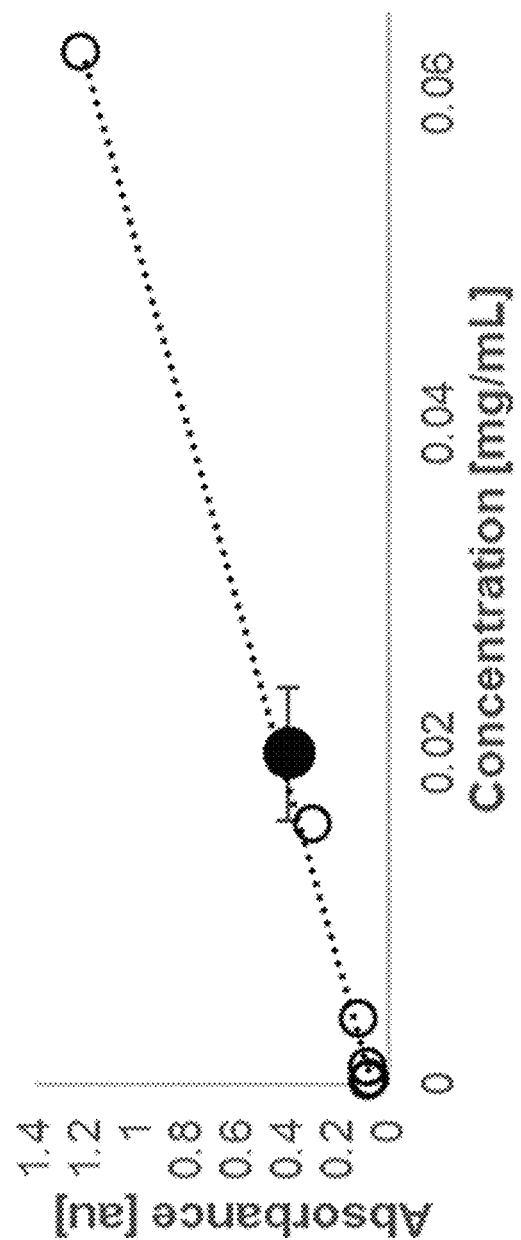
FIG. 4 graphically represents a calibration curve for the delivery of acetaminophen with a drug delivery device in accordance with certain aspects of the invention. The concentrations of diffused drug were found by comparing the data against the calibration curve of absorbance versus known concentrations. The spectrophotometer reading was obtained using $\lambda=243$ nm (maximum for acetaminophen). Data are presented as average±standard deviation.

In experiments leading to the present invention, a test drug (powdered acetaminophen) was placed in the reservoir of a drug delivery device configured similar to the representations of FIGS. 1 and 2 and closed by a seal formed of a thermosensitive wax. The drug was released by melting the seal with heat generated by an inductively-coupled heating element. Spectrophotometric analysis was performed to measure the concentration of drug released. Results of the experiments evidenced that the experimental device was able to successfully diffuse the drug to the surroundings of the device when current was supplied to the heating element via a generator. FIG. 4 contains a calibration curve for acetaminophen and preliminary data. The concentrations of the diffused drug were found by comparing the data against the calibration curve of absorbance versus known concentrations. The spectrophotometer reading was obtained using $\lambda=243$ nm (maximum for acetaminophen). The data in FIG. 4 is presented as average±standard deviation, and the investigation showed that approximately 1 A was sufficient to melt the seal in a timely manner (less than 10 seconds). The device was determined to deliver a drug dose of about 2 to 5 mg.

In another investigation, the time required to heat stainless steel heating elements sized for use in a device of the type represented in FIGS. 1 and 2. The heating elements were inductively heated from a typical human body temperature of 37° C. to a temperature of 42° C., and observed with an infrared (IR) camera. The average time for the five heating elements was about 10 seconds.

Figure 5:
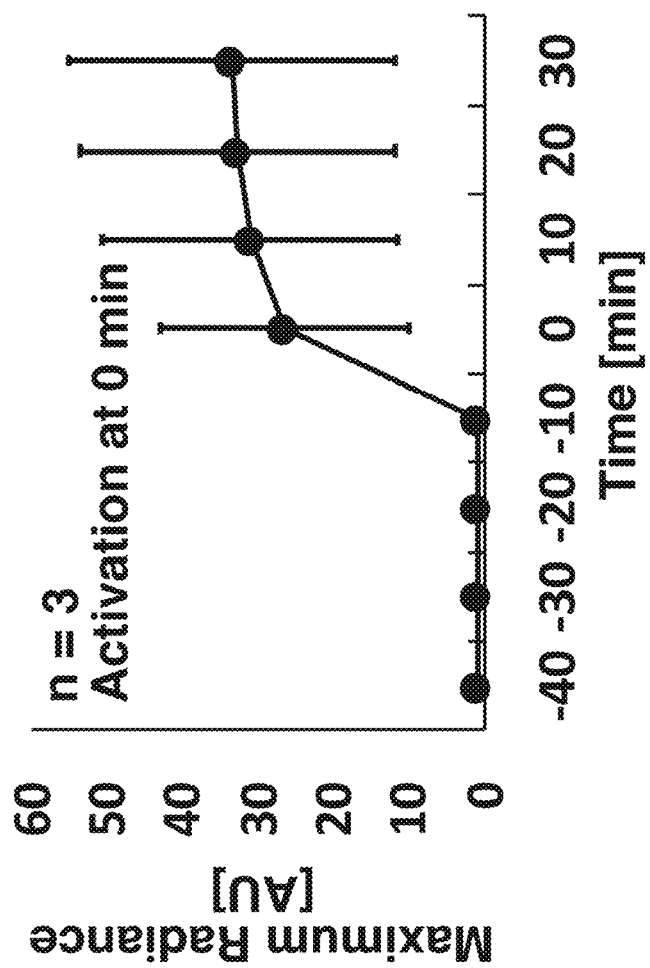
FIG. 5 is a graph plotting normalized radiance values from fluorescent images of three mice, each the recipient of a subcutaneously-implanted drug delivery device.

Preliminary in vivo investigations were also carried out to verify successful activation and passive diffusion of a drug from devices of the type represented in FIGS. 1 and 2. For these investigations, incisions were made in the backs and down the necks of three male mice (C57BL). The skin was lifted and separated from the underlying tissue using forceps and surgical scissors, followed by implantation of the devices. Subcutaneous space was created within each incision to provide space surrounding each device for diffusion of indocyanine green (ICG) dye placed in the reservoirs of the devices. The mice were imaged every minute for forty minutes prior to activation of the devices, which were activated using a magnetic field generated by a coil placed above the skin of each mouse. The coil was supplied with 250 kHz 25 mVpp with a gain of 10 for sixty seconds to minimize the heating of the outer coil. The mice were then imaged for forty minutes post-activation. The normalized radiance values from fluorescent images of the mice are plotted in FIG. 5, and evidence that no leakage occurred from the devices in the first forty minutes after implantation and prior to activation. Post-activation, the radiance of the drug signal exponentially increased and stabilized in about ten minutes, evidencing that the devices exhibited a burst release profile as a result of the rapid melting of their temporary seals, contrary to slow-release profiles usually observed with drug delivery implants.

While the invention has been described in terms of particular embodiments and investigations, it should be apparent that alternatives could be adopted by one skilled in the art. For example, the drug delivery device 10 and its components could differ in appearance and construction from the embodiments described herein and shown in the drawings, functions of certain components of the device 10 could be performed by components of different construction but capable of a similar (though not necessarily equivalent) function, parameters such as temperatures and durations could be modified, and appropriate materials could be substituted for those noted. As such, it should be understood that the above detailed description is intended to describe the particular embodiments represented in the drawings and certain but not necessarily all features and aspects thereof, and to identify certain but not necessarily all alternatives to the embodiments and their described features and aspects. As a nonlimiting example, the invention encompasses additional or alternative embodiments in which one or more features or aspects of a particular embodiment could be eliminated or two or more features or aspects of different embodiments could be combined. Accordingly, it should be understood that the invention is not necessarily limited to any embodiment described herein or illustrated in the drawings, and the phraseology and terminology employed above are for the purpose of describing the illustrated embodiments and investigations and do not necessarily serve as limitations to the scope of the invention. Therefore, the scope of the invention is to be limited only by the following claims.

The invention claimed is:

1. A system comprising:
   an implantable drug delivery device for delivering at least one drug to a living body, the device comprising:
   a housing having at least one opening;
   a reservoir within the housing adapted to contain the at least one drug;
   a temporary seal closing the at least one opening of the housing; and
   a tubular-shaped ferrous heating element incorporated into the housing so as to be within the reservoir and in thermal contact with the temporary seal, the heating element configured to generate heat in response to electrical current supplied thereto via application of an oscillating magnetic field to at least partially melt the temporary seal and release the at least one drug within the reservoir through the at least one opening of the housing;
   an apparatus configured to apply the oscillating magnetic field to the implantable drug delivery device; and
   one or more sensors configured to attach to or be carried in proximity to the living body and to monitor the living body to detect changes in body functions of the living body indicative of a condition;
   wherein the apparatus is configured to automatically apply the oscillating magnetic field to the implantable drug delivery device such that the heating element generates heat sufficient to at least partially melt the temporary seal and release the at least one drug from the reservoir in response to the one or more sensors detecting the changes in the body functions of the living body indicative of the condition.

2. The system of claim 1, wherein the implantable drug delivery device contains the at least one drug within the reservoir.

3. The system of claim 2, wherein the at least one drug is naloxone, epinephrine, or naltrexone.

4. The system of claim 2, wherein the at least one drug is contained within the reservoir under pressure so as to be forcibly ejected from the reservoir once the temporary seal has at least partially melted.

5. The system of claim 1, wherein the temporary seal is formed of a biocompatible cross-linked polymer.

6. The system of claim 1, wherein the apparatus is further configured to be manually operated to apply the oscillating magnetic field.

7. The system of claim 1, wherein the apparatus includes a radio frequency generator configured to externally generate an emission that wirelessly energizes the heating element to heat the temporary seal.

8. The system of claim 1, wherein the implantable drug delivery device is sized and configured to be subcutaneously implanted.

9. The system of claim 1, wherein the one or more sensors includes a temperature sensor configured to monitor a body temperature of the living body.

10. The system of claim 1, wherein the condition is an opioid overdose and the at least one drug includes an anti-overdose drug configured to treat the opioid overdose.

11. A method of using the implantable drug delivery device of claim 1 to deliver the at least one drug to the living body, the method comprising:
   placing the at least one drug in the reservoir of the housing;
   implanting the implantable drug delivery device in the living body; and
   energizing the heating element in response to a reaction of the living body, the heating element sufficiently melting the temporary seal to release the at least one drug into the living body through the at least one opening in the housing.

12. The method of claim 11, wherein the reaction of the living body is a physiological reaction to an opioid overdose.

13. The method of claim 12, wherein the physiological reaction is a rise in body temperature.

* * * * *